United States Patent
Lange

(10) Patent No.: US 10,952,638 B2
(45) Date of Patent: Mar. 23, 2021

(54) SYSTEM AND METHOD FOR MONITORING RESPIRATORY RATE AND OXYGEN SATURATION

(71) Applicant: ChroniSense Medical Ltd., Yokneam (IL)

(72) Inventor: Daniel H. Lange, Kfar Vradim (IL)

(73) Assignee: ChroniSense Medical Ltd., Yokneam (IL)

(*) Notice: Subject to any disclaimer, the term of this patent is extended or adjusted under 35 U.S.C. 154(b) by 291 days.

(21) Appl. No.: 16/132,224

(22) Filed: Sep. 14, 2018

(65) Prior Publication Data
US 2019/0015014 A1    Jan. 17, 2019

Related U.S. Application Data

(63) Continuation-in-part of application No. 14/983,118, filed on Dec. 29, 2015, now Pat. No. 10,687,742.
(Continued)

(51) Int. Cl.
*A61B 5/08* (2006.01)
*A61B 5/1455* (2006.01)
(Continued)

(52) U.S. Cl.
CPC .......... *A61B 5/0816* (2013.01); *A61B 5/0015* (2013.01); *A61B 5/0205* (2013.01);
(Continued)

(58) Field of Classification Search
CPC ... A61B 5/0816; A61B 5/0015; A61B 5/7465; A61B 5/0205; A61B 5/7235; A61B 5/1455
See application file for complete search history.

(56) References Cited

U.S. PATENT DOCUMENTS 3,885,552 A    5/1975  Kennedy
3,898,984 A    8/1975  Mandel et al.
(Continued)

FOREIGN PATENT DOCUMENTS

CN    1335756 A    2/2002
CN    106901747 A    6/2017
(Continued)

OTHER PUBLICATIONS

Arza et al., "Pulse Transit Time and Pulse Width as Potential Measure for estimating Beat-to-Beat Systolic and Diastolic Blood Pressure", Computing in Cardiology 2013, pp. 887-890.
(Continued)

*Primary Examiner* — Eric F Winakur
(74) *Attorney, Agent, or Firm* — Carr & Ferrell LLP

(57) ABSTRACT

A method and system for monitoring respiratory rate of a patient is provided. An example system includes a wearable device configured to be disposed around a wrist of the patient. The wearable device may include a gyroscope to measure a gyroscope signal indicative of a motion of the patient. The system may further include a processor communicatively coupled to the gyroscope. The processor can be configured to perform a spectral analysis of the gyroscope signal to obtain a spectrum in a pre-determined range. The pre-determined range may cover a normal respiratory rate range. The processor can be further configured to determine a position of a peak in the spectrum to obtain a value for the respiratory rate. The processor can be further configured to provide, based on the value of the respiratory rate, a message regarding a health status of the patient.

20 Claims, 11 Drawing Sheets

Related U.S. Application Data which is a continuation-in-part of application No. 14/738,636, filed on Jun. 12, 2015, and a continuation-in-part of application No. 14/738,666, filed on Jun. 12, 2015, application No. 14/983,118, which is a continuation-in-part of application No. 14/738,666, filed on Jun. 12, 2015, and a continuation-in-part of application No. 14/738,711, filed on Jun. 12, 2015, now Pat. No. 10,470,692, application No. 16/132,224, which is a continuation-in-part of application No. 14/738,711, filed on Jun. 12, 2015, now Pat. No. 10,470,692, said application No. 14/983,118 is a continuation-in-part of application No. 14/738,666, filed on Jun. 12, 2015, which is a continuation-in-part of application No. 14/738,636, filed on Jun. 12, 2015.

(51) Int. Cl.
| | | |
|---|---|---|
| *A61B 5/00* | (2006.01) | |
| *A61B 5/0205* | (2006.01) | |
| *A61B 5/026* | (2006.01) | |
| *A61B 5/11* | (2006.01) | |
| *A61B 5/0404* | (2006.01) | |

(52) U.S. Cl.
CPC .......... *A61B 5/0806* (2013.01); *A61B 5/1455* (2013.01); *A61B 5/14551* (2013.01); *A61B 5/681* (2013.01); *A61B 5/0261* (2013.01); *A61B 5/0404* (2013.01); *A61B 5/0803* (2013.01); *A61B 5/11* (2013.01); *A61B 5/486* (2013.01); *A61B 5/7235* (2013.01); *A61B 5/7275* (2013.01); *A61B 5/746* (2013.01); *A61B 5/7465* (2013.01); *A61B 2562/046* (2013.01)

(56) References Cited

U.S. PATENT DOCUMENTS

| | | | |
|---|---|---|---|
| 4,331,154 | A | 5/1982 | Broadwater et al. |
| 4,732,158 | A | 3/1988 | Sadeh |
| 4,802,486 | A | 2/1989 | Goodman et al. |
| 5,050,612 | A | 9/1991 | Matsumura |
| 5,316,008 | A | 5/1994 | Suga et al. |
| 5,503,148 | A | 4/1996 | Pologe et al. |
| 5,692,505 | A | 12/1997 | Fouts |
| 6,047,203 | A | 4/2000 | Sackner et al. |
| 6,139,494 | A | 10/2000 | Cairnes |
| 6,527,725 | B1 | 3/2003 | Inukai et al. |
| 7,184,809 | B1 | 2/2007 | Sterling et al. |
| 7,479,111 | B2 | 1/2009 | Zhang et al. |
| 7,544,168 | B2 | 6/2009 | Nitzan |
| 7,738,935 | B1 | 6/2010 | Turcott |
| 8,172,764 | B2 | 5/2012 | Gregson et al. |
| 8,602,997 | B2 | 12/2013 | Banet et al. |
| 8,866,606 | B1 | 10/2014 | Will et al. |
| 10,470,692 | B2 | 11/2019 | Lange et al. |
| 2001/0005773 | A1 | 6/2001 | Larsen et al. |
| 2001/0029326 | A1 | 10/2001 | Diab et al. |
| 2002/0095077 | A1 | 7/2002 | Swedlow et al. |
| 2002/0133068 | A1 | 9/2002 | Huiku |
| 2003/0009091 | A1 | 1/2003 | Edgar, Jr. et al. |
| 2003/0036685 | A1 | 2/2003 | Goodman |
| 2003/0065269 | A1 | 4/2003 | Vetter et al. |
| 2003/0109776 | A1 | 6/2003 | Jacques |
| 2003/0163033 | A1 | 8/2003 | Dekker |
| 2004/0215095 | A1 | 10/2004 | Lee et al. |
| 2005/0070775 | A1 | 3/2005 | Chin et al. |
| 2005/0215913 | A1 | 9/2005 | Lee et al. |
| 2005/0281439 | A1 | 12/2005 | Lange |
| 2006/0074322 | A1 | 4/2006 | Nitzan |
| 2006/0264767 | A1 | 11/2006 | Shennib |
| 2007/0142720 | A1 | 6/2007 | Ridder et al. |
| 2007/0191725 | A1 | 8/2007 | Nelson |
| 2008/0146954 | A1 | 6/2008 | Bojovic et al. |
| 2008/0208069 | A1 | 8/2008 | John et al. |
| 2008/0214961 | A1 | 9/2008 | Matsumoto et al. |
| 2008/0221419 | A1 | 9/2008 | Furman |
| 2008/0255433 | A1 | 10/2008 | Prough et al. |
| 2009/0024011 | A1 | 1/2009 | Huiku |
| 2009/0163821 | A1 | 6/2009 | Sola I Caros et al. |
| 2009/0247848 | A1 | 10/2009 | Baker, Jr. |
| 2010/0016694 | A1 | 1/2010 | Martin et al. |
| 2010/0179438 | A1 | 7/2010 | Heneghan et al. |
| 2010/0217144 | A1 | 8/2010 | Brian |
| 2010/0298656 | A1 | 11/2010 | McCombie et al. |
| 2010/0312079 | A1 | 12/2010 | Larsen et al. |
| 2010/0324384 | A1 | 12/2010 | Moon et al. |
| 2011/0060200 | A1 | 3/2011 | Bernreuter |
| 2011/0066051 | A1 | 3/2011 | Moon et al. |
| 2011/0077486 | A1 | 3/2011 | Watson et al. |
| 2011/0082355 | A1 | 4/2011 | Eisen et al. |
| 2011/0201946 | A1 | 8/2011 | Turcott |
| 2011/0224564 | A1 | 9/2011 | Moon et al. |
| 2011/0257551 | A1 | 10/2011 | Banet et al. |
| 2012/0190944 | A1 | 7/2012 | Thaveeprungsriporn et al. |
| 2012/0238834 | A1 | 9/2012 | Hornick |
| 2013/0231947 | A1 | 9/2013 | Shusterman |
| 2013/0296665 | A1 | 11/2013 | Kassim et al. |
| 2013/0296666 | A1 | 11/2013 | Kumar et al. |
| 2013/0296673 | A1 | 11/2013 | Thaveeprungsriporn et al. |
| 2013/0310700 | A1 | 11/2013 | Wiard et al. |
| 2013/0338536 | A1 | 12/2013 | He et al. |
| 2014/0043164 | A1 | 2/2014 | Eschelman et al. |
| 2014/0088449 | A1 | 3/2014 | Nearing et al. |
| 2014/0142445 | A1 | 5/2014 | Banet et al. |
| 2014/0206948 | A1 | 7/2014 | Romem |
| 2014/0275888 | A1 | 9/2014 | Wegerich et al. |
| 2014/0278229 | A1 | 9/2014 | Hong et al. |
| 2015/0109125 | A1 | 4/2015 | Kaib et al. |
| 2015/0148622 | A1 | 5/2015 | Moyer et al. |
| 2015/0157220 | A1 | 6/2015 | Fish et al. |
| 2015/0157262 | A1 | 7/2015 | Schuessler |
| 2015/0196257 | A1 | 7/2015 | Yousefi et al. |
| 2015/0265161 | A1* | 9/2015 | Hernandez ........... A61B 5/0816 600/476 |
| 2015/0272510 | A1 | 10/2015 | Chin |
| 2015/0313484 | A1 | 11/2015 | Burg et al. |
| 2015/0320328 | A1 | 11/2015 | Albert |
| 2015/0342538 | A1 | 12/2015 | St. Pierre et al. |
| 2015/0366469 | A1 | 12/2015 | Harris et al. |
| 2015/0366492 | A1 | 12/2015 | De Haan et al. |
| 2015/0366518 | A1 | 12/2015 | Sampson |
| 2016/0000376 | A1 | 1/2016 | Murray et al. |
| 2016/0022220 | A1 | 1/2016 | Lee et al. |
| 2016/0089033 | A1 | 3/2016 | Saponas et al. |
| 2016/0093205 | A1 | 3/2016 | Boyer |
| 2016/0120434 | A1 | 5/2016 | Park et al. |
| 2016/0183846 | A1* | 6/2016 | Derkx ................. A61B 5/0816 600/534 |
| 2016/0270668 | A1 | 9/2016 | Gil |
| 2016/0270677 | A1 | 9/2016 | Lin |
| 2016/0360971 | A1 | 12/2016 | Gross et al. |
| 2016/0360974 | A1 | 12/2016 | Lange |
| 2016/0360986 | A1 | 12/2016 | Lange |
| 2016/0361003 | A1 | 12/2016 | Lange et al. |
| 2016/0361004 | A1 | 12/2016 | Lange et al. |
| 2017/0014037 | A1 | 1/2017 | Coppola et al. |
| 2017/0156593 | A1 | 6/2017 | Ferber et al. |
| 2017/0202459 | A1 | 7/2017 | Cao |
| 2017/0258406 | A1 | 9/2017 | Lange |
| 2018/0098705 | A1 | 4/2018 | Chaturvedi et al. |
| 2018/0132794 | A1 | 5/2018 | Lange |
| 2018/0247713 | A1 | 8/2018 | Rothman |

FOREIGN PATENT DOCUMENTS

| | | |
|---|---|---|
| CN | 107920786 A | 4/2018 |
| CN | 107920786 B | 12/2020 |
| EP | 2430975 A1 | 3/2012 |
| EP | 3307146 A1 | 4/2018 |
| EP | 3307150 A1 | 4/2018 |

(56) References Cited

FOREIGN PATENT DOCUMENTS

| | | |
|---|---|---|
| EP | 3307162 A1 | 4/2018 |
| EP | 3493734 A1 | 6/2019 |
| EP | 3307146 B1 | 11/2020 |
| WO | WO0047108 A1 | 8/2000 |
| WO | WO2001015597 A1 | 3/2001 |
| WO | WO2006048701 A2 | 5/2006 |
| WO | WO2014022906 A1 | 2/2014 |
| WO | WO2015047015 A1 | 4/2015 |
| WO | WO2015070030 A1 | 5/2015 |
| WO | WO2015197383 A1 | 12/2015 |
| WO | WO2016110804 A1 | 7/2016 |
| WO | WO2016199121 A1 | 12/2016 |
| WO | WO2016199122 A1 | 12/2016 |
| WO | WO2016199123 A1 | 12/2016 |
| WO | WO2016199124 A1 | 12/2016 |
| WO | WO2017141131 A1 | 8/2017 |
| WO | WO2017158585 A1 | 9/2017 |
| WO | WO2018025257 A1 | 2/2018 |
| WO | WO2018085563 A1 | 5/2018 |
| WO | WO2019130296 A1 | 7/2019 |
| WO | WO2020053858 A1 | 3/2020 |

OTHER PUBLICATIONS

Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.

International Search Report and Written Opinion dated Jul. 11, 2016 in Patent Cooperation Treaty Application No. PCT/IL2016/050511 filed May 15, 2016, 19 pages.

International Search Report and Written Opinion dated Aug. 18, 2016 in Patent Cooperation Treaty Application No. PCT/IL2016/050514 filed May 15, 2016, 20 pages.

International Search Report and Written Opinion dated Aug. 29, 2016 in Patent Cooperation Treaty Application No. PCT/IL2016/050513 filed May 15, 2016, 18 pages.

Patent Cooperation Treaty Application No. PCT/IL2016/050512, "International Search Report" and "Written Opinion of the International Searching Authority," dated Sep. 18, 2016, 9 pages.

"International Search Report" and "Written Opinion of the International Searching Authority," Patent Cooperation Treaty Application No. PCT/IL2017/050242, dated Jun. 13, 2017, 12 pages.

Abtahi, Farhad, "Feasibility of Fetal EEG Recording," Master's Thesis, Department of Signal and System, Chalmers Universtiy of Technology, Gothenburg, Sweden, Jan. 1, 2011, 51 pages.

Richardson, Kelly et al., "Electrocardiographic damage scores and cardiovascular mortality," American Heart Journal vol. 149, No. 3, Mar. 1, 2005, pp. 458-463.

"International Search Report" and "Written Opinion of the International Searching Authority," Patent Cooperation Treaty Application No. PCT/IL2017/050826, dated Oct. 23, 2017, 9 pages.

"Extended European Search Report," European Patent Application No. 16807014.2, dated Oct. 22, 2018, 8 pages.

"Extended European Search Report," European Patent Application No. 16807015.9, dated Jan. 21, 2019, 10 pages.

Gözde, Ateş et al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.

"Extended European Search Report," European Patent Application No. 16807013.4, dated Jan. 17, 2019, 7 pages.

"Extended European Search Report," European Patent Application No. 17836517.7, dated Feb. 25, 2020, 5 pages.

"Office Action," Chinese Patent Application No. 201680042023.6, dated Mar. 20, 2020, 10 pages.

"International Search Report" and "Written Opinion of the International Searching Authority," Patent Cooperation Treaty Application No. PCT/IL2018/051384, dated Mar. 14, 2019, 15 pages.

"Office Action," European Patent Application No. 16807013.4, dated Aug. 27, 2019, 6 pages.

"International Search Report" and "Written Opinion of the International Searching Authority," Patent Cooperation Treaty Application No. PCT/IL2019/051018, dated Dec. 17, 2019, 14 pages.

"Notice of Allowance", European Patent Application No. 17836517.7, dated Oct. 1, 2020, 7 pages.

\* cited by examiner

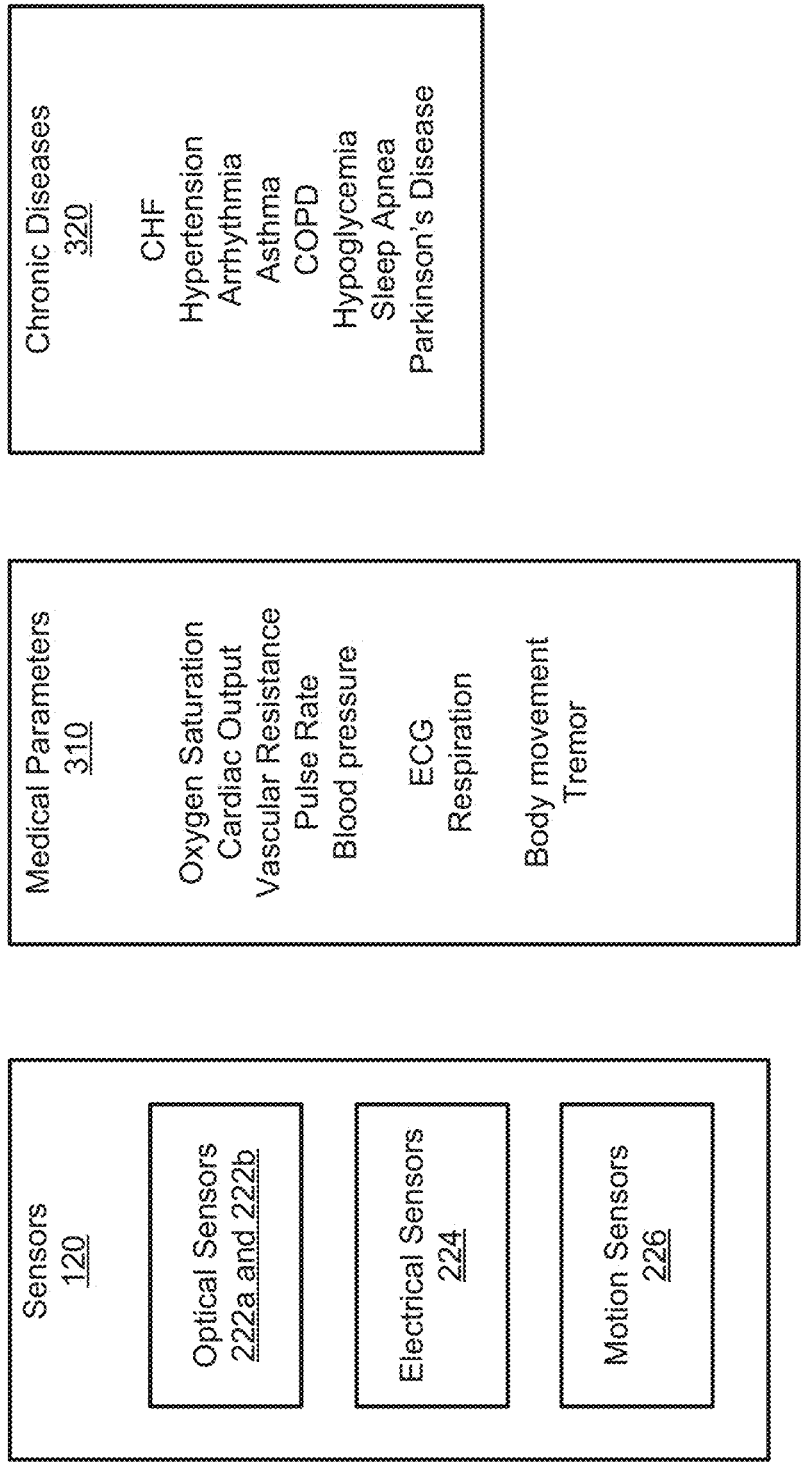

```
┌─────────────────────────────────────────────────────────────┐
│ Measure, at a palmar surface of a wrist of a patient, by a  │
│ first optical sensor of a wearable device configured to be  │
│ disposed around the wrist of the patient, a first red       │
│ wavelength photoplethysmography (PPG) signal and a first    │
│ infrared wavelength PPG signal                              │
│                            910                              │
└─────────────────────────────────────────────────────────────┘
                              ↓
┌─────────────────────────────────────────────────────────────┐
│ Measure, at a dorsal surface of the wrist, by a second      │
│ optical sensor, a second red wavelength PPG signal and a    │
│ second infrared wavelength PPG signal                       │
│                            920                              │
└─────────────────────────────────────────────────────────────┘
                              ↓
┌─────────────────────────────────────────────────────────────┐
│ Determine, by a processor communicatively connected to the  │
│ first optical sensor and the second optical sensor and      │
│ based on the first red wavelength PPG signal and the first  │
│ infrared wavelength PPG signal, a first ratio for obtaining │
│ an oxygen saturation                                        │
│                            930                              │
└─────────────────────────────────────────────────────────────┘
                              ↓
┌─────────────────────────────────────────────────────────────┐
│ Determine, by the processor and based on the second red     │
│ wavelength PPG signal and the second infrared wavelength    │
│ PPG signal, a second ratio for obtaining the oxygen         │
│ saturation                                                  │
│                            940                              │
└─────────────────────────────────────────────────────────────┘
                              ↓
┌─────────────────────────────────────────────────────────────┐
│ Determine, by the processor and based on the first ratio    │
│ and the second ratio, a third ratio for obtaining an oxygen │
│ saturation                                                  │
│                            950                              │
└─────────────────────────────────────────────────────────────┘
                              ↓
┌─────────────────────────────────────────────────────────────┐
│ Determine, by the processor and based on the third ratio,   │
│ a value of the oxygen saturation                            │
│                            960                              │
└─────────────────────────────────────────────────────────────┘
                              ↓
┌─────────────────────────────────────────────────────────────┐
│ Provide, by the processor and based on the value of the     │
│ oxygen saturation, a message regarding a health status of   │
│ the patient                                                 │
│                            970                              │
└─────────────────────────────────────────────────────────────┘
```

FIG. 9

```
┌─────────────────────────────────────────────────────────────┐
│ Provide, by a gyroscope of a wearable device disposed on a  │
│ wrist of a patient, a gyroscope signal indicative of a      │
│ motion of the patient, the gyroscope being communicatively  │
│ coupled with a processor                                    │
│                          1010                               │
└─────────────────────────────────────────────────────────────┘
                              │
                              ▼
┌─────────────────────────────────────────────────────────────┐
│ Perform, by the processor, a spectral analysis of the       │
│ gyroscope signal to obtain a spectrum in a pre-determined   │
│ frequency range, the pre-determined frequency range         │
│ covering a normal respiratory rate range                    │
│                          1020                               │
└─────────────────────────────────────────────────────────────┘
                              │
                              ▼
┌─────────────────────────────────────────────────────────────┐
│ Determine, by the processor, a position of a peak in the    │
│ spectrum to obtain a value for a respiratory rate           │
│                          1030                               │
└─────────────────────────────────────────────────────────────┘
                              │
                              ▼
┌─────────────────────────────────────────────────────────────┐
│ Provide, by the processor and based on the value of the     │
│ respiratory rate, a message regarding the health status of  │
│ the patient                                                 │
│                          1040                               │
└─────────────────────────────────────────────────────────────┘
```

FIG. 10

SYSTEM AND METHOD FOR MONITORING RESPIRATORY RATE AND OXYGEN SATURATION

CROSS-REFERENCE TO RELATED APPLICATIONS

The present application is a Continuation-in-Part of U.S. patent application Ser. No. 14/738,666, titled "Monitoring Health Status of People Suffering from Chronic Diseases," filed on Jun. 12, 2015, a Continuation-in-Part of U.S. patent application Ser. No. 14/738,636, titled "Wearable Device Electrocardiogram," filed on Jun. 12, 2015, a Continuation-in-Part of U.S. patent application Ser. No. 14/738,711, titled "Pulse Oximetry," filed on Jun. 12, 2015, and a Continuation-in-Part of U.S. patent application Ser. No. 14/983,118, titled "Using Invariant Factors for Pulse Oximetry," filed on Dec. 29, 2015. U.S. patent application Ser. No. 14/983,118 is a Continuation-in-Part of U.S. patent application Ser. No. 14/738,666, titled "Monitoring Health Status of People Suffering from Chronic Diseases," filed on Jun. 12, 2015, a Continuation-in-Part of U.S. patent application Ser. No. 14/738,636, titled "Wearable Device Electrocardiogram," filed on Jun. 12, 2015, and a Continuation-in-Part of U.S. patent application Ser. No. 14/738,711, titled "Pulse Oximetry," filed on Jun. 12, 2015. All of the disclosures of the aforementioned applications are incorporated herein by reference for all purposes, including all references cited therein.

FIELD

The present application relates to systems and methods for monitoring medical parameters of people, and more specifically to systems and methods for monitoring respiratory rate and oxygen saturation.

BACKGROUND

It should not be assumed that any of the approaches described in this section qualify as prior art merely by virtue of their inclusion in this section.

Monitoring chronic diseases, which includes measuring medical parameters, is central to providing appropriate and timely treatment to patients suffering from such chronic diseases as chronic heart failure, cardiac arrhythmia, chronic obstructive pulmonary disease, asthma, and diabetes. Traditionally, monitoring is carried out and measurements are taken while a patient is hospitalized or in other clinical settings. Appropriate treatment regimens can be based on these measurements, and thus it is highly beneficial to monitor medical parameters of the patient after the patient is released from the hospital. Therefore, the patient can be asked to visit the hospital or clinic periodically for monitoring and adjustment of treatment, if necessary.

However, most often, no measurements are carried out between visits, usually due to the need for trained examiners and medical devices. This is unfortunate, because, between visits, the chronic disease from which the patient suffers can worsen and result in emergency treatment and hospitalization. Furthermore, after receiving repeated courses of emergency hospital treatment, the patient's health condition may degrade and never return to the pre-hospitalization level. Therefore, a technology that allows for at-home measurements of medical parameters can be essential to managing chronic diseases or even saving a patient's life. Early warnings of worsening conditions associated with chronic diseases may prevent unnecessary hospitalizations by providing a preventive treatment and, as a result, reduce financial and human costs of the hospitalization and treatment.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one embodiment of the present disclosure, a system for monitoring medical parameters of a patient is provided. The system may include a wearable device configured to be disposed around a wrist of the patient. The wearable device may include a gyroscope configured to provide a gyroscope signal indicative of a motion of the patient. The system may further include a processor communicatively coupled to the gyroscope. The processor can be configured to perform a spectral analysis of the gyroscope signal to obtain a spectrum in a pre-determined range. The pre-determined range can cover a normal respiratory rate range. The processor can be configured to determine a position of a peak in the spectrum to obtain a value for the respiratory rate. The processor can be configured to provide, based on the value of the respiratory rate, a message regarding a health status of the patient.

Based on the determination that the value of the respiratory rate is outside the normal respiratory range, the processor can provide an alert message regarding the health status of the patient. The spectral analysis can be performed by a method of averaged periodograms. A normal respiratory rate range may include 6 to 18 breaths per minute.

The processor can be configured to determine the strongest amplitude peak in the spectrum to obtain a value for the respiratory rate. The processor can determine that the spectrum includes one or more further peaks with descending amplitudes. The further peaks correspond to frequencies $n*\omega$, wherein $\omega$ is a frequency corresponding to the strongest amplitude peak, and n is a natural number. Based on the determination, the processor may assign $\omega$ to the value of the respiratory rate.

The wearable device may further include a first optical sensor configured to measure, at a palmar surface of the wrist, a first red wavelength photoplethysmography (PPG) signal and a first infrared wavelength PPG signal. The wearable device may further include a second optical sensor configured to measure, at a dorsal surface of the wrist, a second red wavelength PPG signal and a second infrared wavelength PPG signal. The first optical sensor and the second optical sensor can be communicatively coupled to the processor.

The processor can be configured to determine, based on the first red wavelength PPG signal and the first infrared wavelength PPG signal, a first ratio for obtaining an oxygen saturation. The processor can be further configured to determine, based on the second red wavelength PPG signal and the second infrared wavelength PPG signal, a second ratio for obtaining the oxygen saturation. The processor can be further configured to determine, based on the first ratio and the second ratio, a third ratio to be used for obtaining an oxygen saturation. The processor can be further configured to determine, based on the third ratio, a value of the oxygen saturation. The processor can be further configured to provide, based on the value of the oxygen saturation, a message regarding a health status of the patient.

The third ratio can be determined by formula $R=\alpha R_a + (1-\alpha)R_b$, wherein the $\alpha$ is a weight between 0 and 1, the $R_a$ is the first ratio, and the $R_b$ is the second ratio. The weight $\alpha$ can be a function of a perfusion index. The perfusion index can be determined based on the second red wavelength PPG signal or the second infrared wavelength PPG signal. The weight $\alpha$ increases when the perfusion index increases. A shape of the function is pre-determined during a calibration process.

The first optical sensor can be configured to measure the first red wavelength PPG signal and the first infrared wavelength PPG signal substantially near a radial artery of the wrist.

According to another example embodiment of the present disclosure, a method for monitoring medical parameters of a patient is provided. The method may include providing, by a gyroscope integrated into a wearable device configured to be worn around a wrist of a patient, a gyroscope signal indicative of a motion of the patient. The method may further include performing, by the processor communicatively coupled with the gyroscope, a spectral analysis of the gyroscope signal to obtain a spectrum in a pre-determined range. The pre-determined range may cover a normal respiratory rate range. The method may further include determining, by the processor, a position of a peak in the spectrum to obtain a value for a respiratory rate. The method may further include providing, by the processor and based on the value of the respiratory rate, a message regarding a health status of the patient.

The method can include measuring at a palmar surface of the wrist of the patient, by a first optical sensor of the wearable device, a first red wavelength PPG signal and a first infrared wavelength PPG signal. The method may include measuring at a dorsal surface of the wrist, by a second optical sensor of the wearable device, a second red wavelength PPG signal and a second infrared wavelength PPG signal. The first optical sensor and the second optical sensor can be communicatively connected to the processor.

The method may further include determining, by a processor and based on the first red wavelength PPG signal and the first infrared wavelength PPG signal, a first ratio for obtaining an oxygen saturation.

The method may include determining, by the processor and based on the second red wavelength PPG signal and the second infrared wavelength PPG signal, a second ratio to be used for obtaining the oxygen saturation. The method may further include determining, by the processor and based on the first ratio and the second ratio, a third ratio for obtaining an oxygen saturation. The method may further include determining, by the processor and based on the third ratio, a value of the oxygen saturation. The method may further include providing, by the processor based on the value of the oxygen saturation, a message regarding a health status of the patient.

According to another example embodiment of the present disclosure, the steps of the method for monitoring medical parameters of a patient can be stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements and in which:

FIG. 3 is a block diagram illustrating example sensors, example medical parameters, and example chronic diseases.

FIG. 9 is a flow chart showing steps of an example method for monitoring a respiratory rate.

FIG. 10 is a flow chart diagram illustrating an example method for monitoring respiratory rate of a patient.

DETAILED DESCRIPTION

Figure 1:
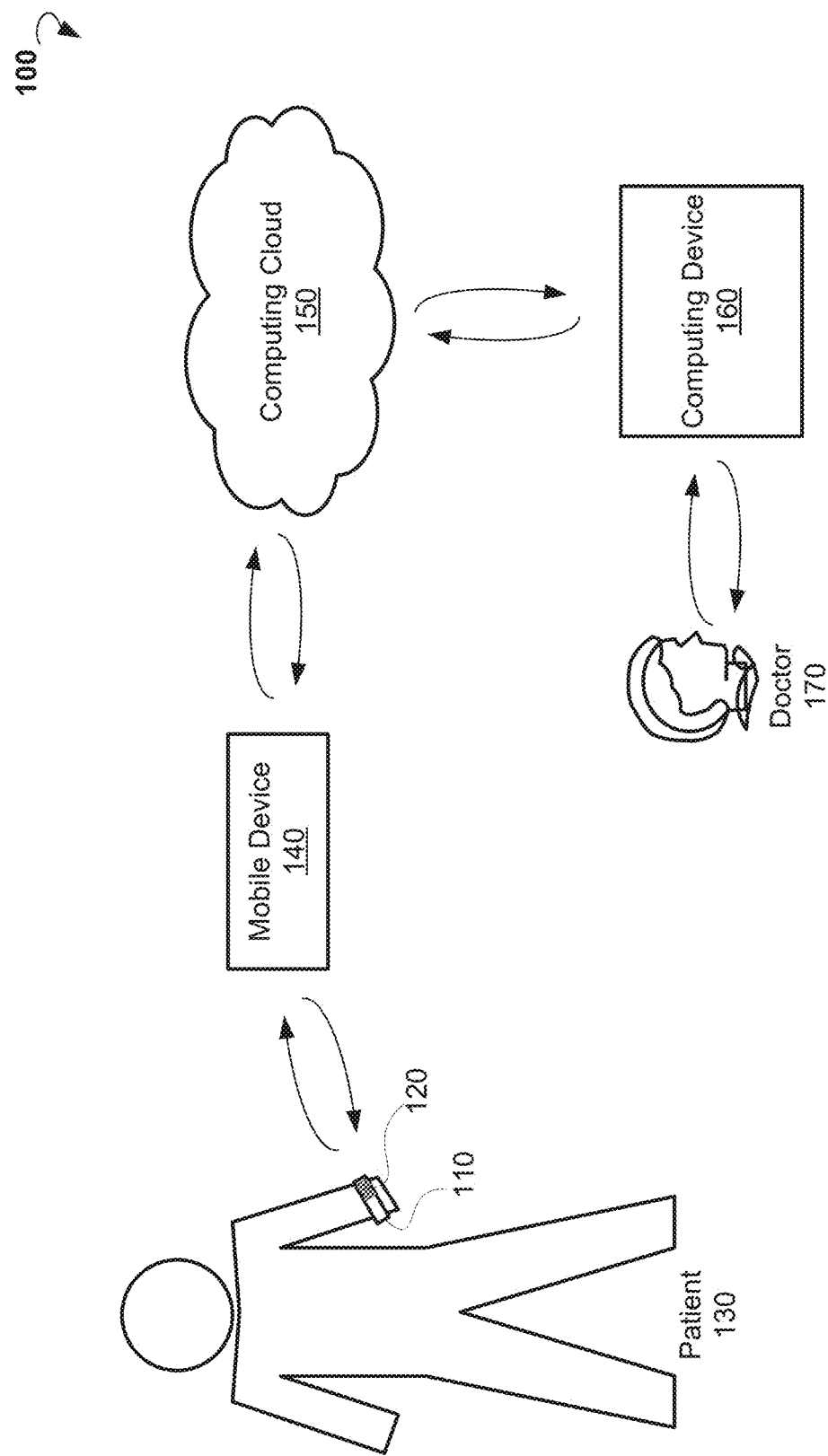
FIG. 1 is a block diagram showing an example system for monitoring medical parameters of a patient.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for monitoring medical parameters of people suffering from chronic diseases. Embodiments of the present disclosure can allow measuring medical parameters of a patient in a non-intrusive manner while, for example, the patient is at home, at work, outdoors, traveling, and at other stationary or mobile environments. Some example embodiments can provide for a wearable device (e.g., a wristband, a watch, or a bracelet) that includes sensors configured to measure medical parameters such as, for example, oxygen saturation, respiratory rate, and the like. The measurements can be taken during daytime and nighttime for days, weeks, months, and years. The medical parameters can be analyzed to determine trends in the medical parameters and to determine whether the severity of the patient's chronic disease (e.g., a heart disease, diabetes, lung disease, and so on) worsens or improves. Embodiments of the present technology may facilitate a rapid reaction to provide an appropriate and timely treatment for the patient. The early treatment may allow taking timely preventive measures to avoid worsening of the patient's condition to the point of requiring an emergency hospitalization and associated expensive medical treatment.

According to various example embodiments, a method for monitoring medical parameters of a patient can include measuring at a palmar surface of a wrist of the patient, by a first optical sensor of a wearable device configured to be disposed around the wrist of the patient, a first red wavelength PPG signal and a first infrared wavelength PPG signal. The method may include measuring from a dorsal surface of the wrist, by a second optical sensor, a second red wavelength PPG signal and a second infrared wavelength PPG signal. The method may also include determining, by a processor communicatively connected to the first optical sensor and the second optical sensor and based on the first red wavelength PPG signal and the first infrared wavelength PPG signal, a first ratio for obtaining an oxygen saturation.

The method may include determining, by the processor and based on the second red wavelength PPG signal and the second infrared wavelength PPG signal, a second ratio to be used to obtain the oxygen saturation. The method may further include determining, by the processor and based on the first ratio and the second ratio, a third ratio to be used to obtain an oxygen saturation. The method may further include determining, by the processor and based on the third ratio, a value of the oxygen saturation. The method may further include providing, by the processor based on the value of the oxygen saturation, a message regarding a health status of the patient.

The method may further include providing, by a gyroscope communicatively coupled with the processor and disposed in the wearable device, a gyroscope signal indicative of motion of the patient. The method may further include performing, by the processor, a spectral analysis of the gyroscope signal to obtain a spectrum in a pre-determined range. The pre-determined range may cover a normal respiratory rate range. The method may further include determining, by the processor, a position of a peak in the spectrum to obtain a value for a respiratory rate. The method may further include determining, by the processor, that the value of the respiratory rate is outside of the normal respiratory rate range. If the value of the respiratory rate is outside of the normal respiratory rate range, the method may further include providing, by the processor, an alert message regarding the health status of the patient.

Referring now to FIG. 1, an example system 100 for monitoring a patient's health status is shown. The system 100 includes at least a wearable device 110. The wearable device may include sensors 120. In some embodiments, the wearable device 110 can be worn by a patient 130, for example on a wrist, for an extended period of time. The wearable device 110 can be carried out as a watch, a bracelet, a wristband, and the like.

The wearable device 110 can be configured to constantly collect, via sensors 120, sensor data from a patient 130. In some embodiments, based on the sensor data, a processor of the wearable device 110 can be configured to obtain, based on the sensor data, medical parameters associated with the patient 130. The medical parameters can be analyzed to obtain changes (trends) in medical parameters over time. Based on the changes, one or more conclusions regarding severity of one or more chronic diseases can be obtained. The processor of the wearable device 110 can be configured to send, via a communication module of the wearable device 110, messages regarding a current health status to a computing device of the patient, a relative, a caretaker of the patient, or a doctor treating the patient. The message to the patient may include an advice to see a doctor and/or take medicine. The processor of the wearable device 110 can display the message on a graphical display system of the wearable device 110.

In some embodiments, the system 100 includes a mobile device 140. The mobile device 140 can be communicatively coupled to the wearable device 110. In various embodiments, the mobile device 140 is operable to communicate with the wearable device 110 via a wireless connection such as, for example, Wi-Fi, Bluetooth, Infrared (IR), and the like. The mobile device 140 can include a mobile phone, a smart phone, a phablet, a tablet computer, a notebook, and so forth. The mobile device 140 can be configured to receive the sensor data and medical parameters from the mobile device 140. In certain embodiments, a processor of the mobile device can be configured to perform analysis of the received sensor data to determine medical parameters. The mobile device 140 can be further configured to provide, via a graphic display system of the mobile device 140, a report regarding current health status. In various embodiments, the mobile device 140 runs one or more applications that provide, via the graphical display system of the mobile device 140, charts and graphics concerning medical parameters of the patient.

In some embodiments, the mobile device 140 can be configured to determine the severity of a health status resulting from the chronic disease from which the patient suffers. The mobile device can be configured to provide the patient with advice to see a medical professional or to take medicine. An alert message regarding health status of the patient can be sent, by the mobile device 140, to a computing device of a doctor, relative, or caretaker of the patient.

In further embodiments, the system 100 may further include a cloud-based computing resource (also referred to as a computing cloud 150). In some embodiments, the cloud-based computing resource includes one or more server farms/clusters comprising a collection of computer servers and is co-located with network switches and/or routers. In certain embodiments, the mobile device 140 and/or wearable device 110 can be communicatively coupled to the computing cloud 150. The mobile device 140 and/or wearable device 110 can be operable to send the sensor data and medical parameters to the computing cloud 150 for further analysis. The computing cloud 150 can be configured to store historical data concerning patient health status including sensor data and medical parameters collected over days, weeks, months, and years. The computing cloud 150 can be configured to run one or more applications to provide reports regarding health status of the patient. A doctor 170 treating the patient may access the reports, for example via a computing device 160, using the Internet or a secure network. In some embodiments, the results of the analysis of the medical parameters can be sent back to the mobile device 140 and/or wearable device 110.

The severity of the health status resulting from a chronic disease can be estimated by computing a deviation or divergence from normal medical parameters of one or more medical parameters being measured at the moment. The normal medical parameters can be specific to the patient and can be derived based on historical data concerning the patient's health status recorded over an extended time period. If the deviation in the medical parameters becomes sufficiently large, the patient can be advised, via a message to the mobile device 140, to take medicine or contact a doctor. In some situations, when the deviation becomes substantial, an alert message can be sent by the mobile device 140 and/or the wearable device 110 to a computing device of a relative, a doctor, or a caretaker of the patient.

It may be desirable for the patient to be assured that the current medical parameters are within an acceptable deviation of the normal medical parameters. For example, when the current medical parameters are normal, the wearable device 110 and/or mobile device 140 can be operable to periodically alert the patient using a pleasant sound. The signal can be provided, for example, every 30 minutes, once every hour, and the like. In certain embodiments, when the medical parameters are within normal values, the mobile device 140 may provide a text message assuring the patient of normal conditions. A haptic feedback component can be used to alert the patient to a health condition, to warn the patient about a specific event concerning treatment of a chronic disease, to remind the patient to take a medicine, if the patient has failed to take the medicine within a predetermined period of time, and so forth. The wearable device 110 may include a haptic feedback functionality for providing the patient with haptic feedback, for example, a tap-in device, to apply a force or vibration to skin of the patient. In further embodiments, the haptic alert can be provided by the mobile device 140. The mobile device 140 can vibrate when the mobile device is in a pocket of the patient or when the mobile device 140 is located on a surface (e.g., a table).

Figure 2:
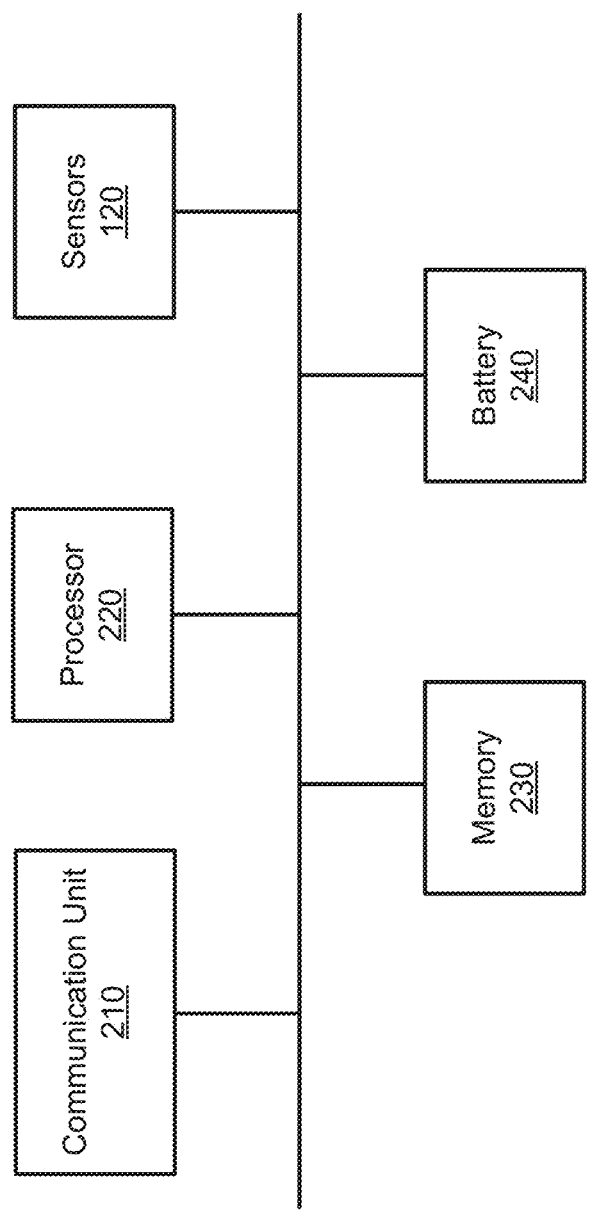
FIG. 2 is a block diagram showing components of an example device for monitoring medical parameters of a patient.

FIG. 2 is a block diagram illustrating components of wearable device 110, according to an example embodiment. The example wearable device 110 may include sensors 120, a communication unit 210, a processor 220, memory 230, and a battery 240.

The communication unit 210 can be configured to communicate with a network such as the Internet, a Wide Area Network (WAN), a Local Area Network (LAN), a cellular network, and so forth, to send a data stream, for example sensor data, medical parameters, and messages concerning the health condition of a patient.

The processor 220 can include hardware and/or software, which is operable to execute computer programs stored in memory 230. The processor 220 can use floating point operations, complex operations, and other operations, including processing and analyzing sensor data.

In some embodiments, the battery 240 is operable to provide electrical power for operation of other components of the wearable device 110. In some embodiments, the battery 240 is a rechargeable battery. In certain embodiments, the battery 240 is recharged using inductive charging technology.

The wearable device 110 may include additional or different components to provide a particular operation or functionality. Similarly, in other embodiments, the wearable device 110 includes fewer components that perform similar or equivalent functions to those depicted in FIG. 2. For example, the wearable device 110 may further include a graphical display system to provide an alert message and display current values of the medical parameters to the patient. The wearable device 110 may also include a haptic device to alert the patient with vibrations. The wearable device 110 may also include an audio signaling device, for example, a beeper or a speaker, to provide sound alerts to the patient.

FIG. 3 is a block diagram showing a list of example sensors 120, a list of example medical parameters 310, and a list of example chronic diseases 320. In various embodiments, the sensors 120 may include optical sensors 222a and 222b, electrical sensors 224, and motion sensors 226. The medical parameters 310, determined based on the sensor data, include, but are not limited to, $SpO_2$ oxygen saturation, tissue oxygen saturation, cardiac output, vascular resistance, pulse rate, blood pressure, respiration, electrocardiogram (ECG) data, respiratory rate, and motion data. The chronic diseases 320, the progression of which can be tracked based on changes of the medical parameters, include but are not limited to congestive heart failure (CHF), hypertension, arrhythmia, asthma, chronic obstructive pulmonary disease (COPD), hypoglycemia, sleep apnea, and Parkinson's disease.

The optical sensors 222a and 222b can be operable to measure medical parameters associated with blood flow in blood vessels using changing absorbance of light at different wavelengths in blood and skin. The data from optical sensors 222a and 222b can be used to determine multiple medical parameters, including but not limited to: $SpO_2$ oxygen saturation, cardiac output, vascular resistance, pulse rate, and respiratory rate. Based on the measurements obtained from optical sensors 222a and 222b, abnormal cardiac rhythms (for example, atrial fibrillation, rapid rhythms, and slow rhythms) can be detected.

In some embodiments, respiratory rate can be derived from a sinus arrhythmia waveform. The sinus arrhythmia waveform can be obtained based on intervals between subsequent heart beats (RR intervals) measured by the optical sensors 222a and 222b using the fact that the rhythm of the heart beats is modulated by human breathing.

The electrical sensors 224 can be operable to obtain ECG activity data of the patient. The ECG activity data includes a characteristic electrically-derived waveform of a heart activity. The ECG data can include a number of components, whose characteristics (timing, amplitude, width, and so forth), alone or in combination, can provide a picture of cardiac and overall health. The ECG data is typically derived by measurements from one or more sets of leads (groups of electrodes comprising grounded circuits), such that the exact characteristics of the resulting waveforms is a function of the electrical and spatial vectors of the electrode positions relative to the heart. While the details of interpretation of the ECG data are too involved to describe succinctly in this disclosure, consideration of each of the component parameters can indicate health status, physical or psychological stress, or trends of disease conditions. Various cardiovascular parameters can be extracted from the ECG alone (such as a heart rate for example), or in combination with other physiological measurements.

According to example embodiments of present disclosure, ECG of the patient can be measured via the electrical sensors 224. Since measurements are taken from a wrist of the patient, electrodes of the electrical sensors 224 should be located very close to each other on a wearable device. Therefore, the ECG data may contain noise. Averaging of several subsequent intervals of the ECG data between heart beats can be used to cancel out noise in ECG data. To determine intervals between two subsequent heart beats, the PPG signals as measured by optical sensors 222a and 222b can be used as a reference. In some embodiments, an arrhythmia analysis can be carried out using the ECG data and data concerning cardiac output and pulse rate.

In some embodiments, motion sensors 226 include an accelerometer, a gyroscope, and an Inertial Measurement Unit (IMU). The motion data obtained via motion sensors 226 can provide parameters of body movement and tremor. The motion data can allow tracking the progression or remission of a motor disease, Parkinson's disease, and physical condition of the patient. In some embodiments, the motion data can be analyzed to determine whether the patient is likely to fall. In some embodiments, the motion data can be analyzed in time domain and frequency domain. By tracking amplitudes of movement of the patient it can be determined if the patient's movements become slower (i.e., the patient becomes sluggish) or the patient is not moving at all. Additionally, according to example embodiments of the present disclosure, the motion data can be analyzed to determine a respiratory rate of the patient.

Figure 4B:
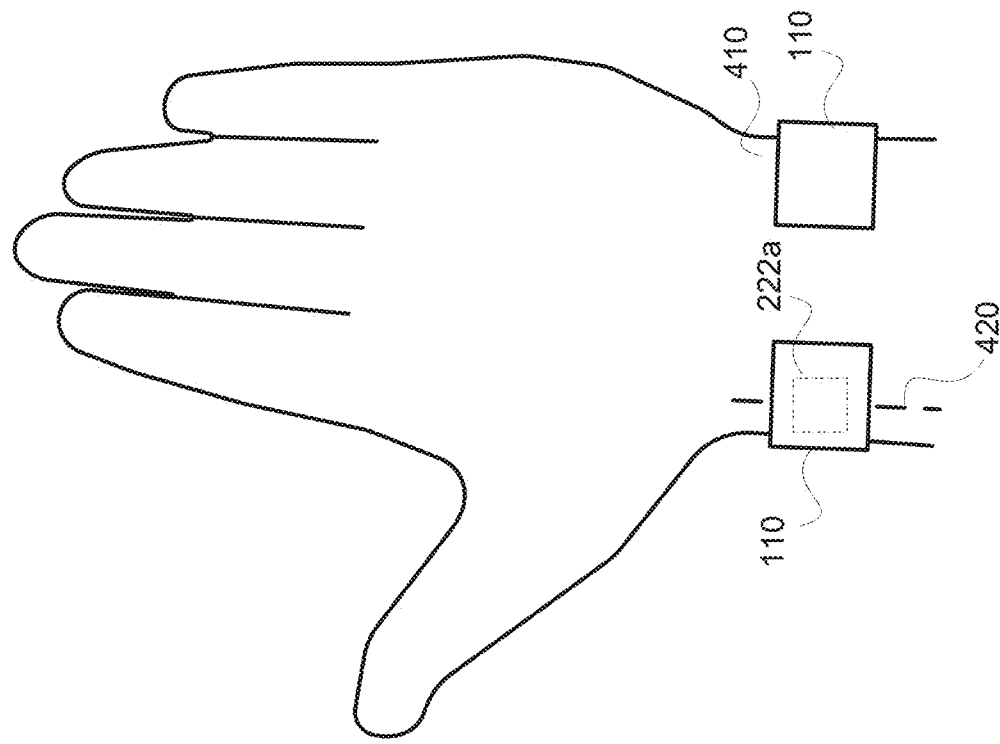
FIGS. 4A and 4B are schematic diagrams illustrating an example device for monitoring medical parameters of a patient.
Figure 4A:
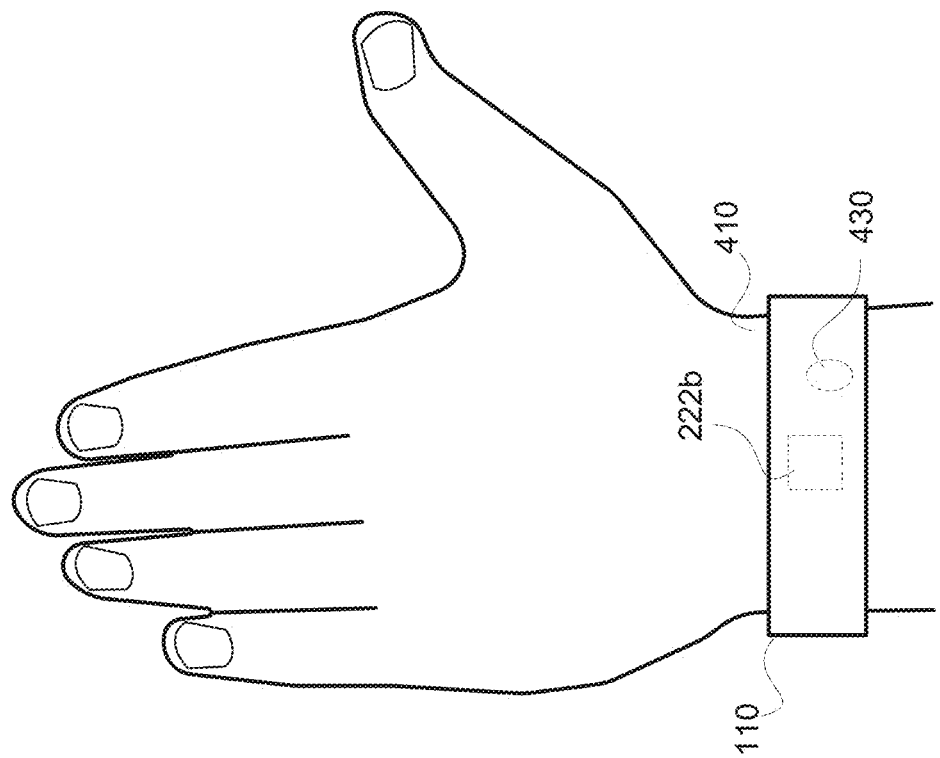

FIG. 4A and FIG. 4B are schematic diagrams illustrating an example wearable device 110. In the examples of FIG. 4A and FIG. 4B, the wearable device 110 can be carried out in a shape of an open bangle. The FIG. 4A shows a dorsal side of a patient's hand 410 and the wearable device 110 placed on the patient's wrist. FIG. 4B shows a palmar side of the patient's hand 410 and wearable device 110. The wearable device 110 can be designed to apply pressure at an area of skin surface covering a radial artery 420. In comparison to wristbands and straps, an open bangle may be more comfortable to wear by a patient since no pressure is applied to the middle area inside the wrist.

The wearable device 110 can include optical sensors 222a and 222b located on an inner side of the wearable device 110. When the wearable device 110 is worn on the patient's hand, the inner side of the wearable device 110 can be in continuous contact with a surface of the skin of the patient's hand 410.

When the wearable device 110 is disposed around a wrist of patient's hand 410, the optical sensor 222a is located as close as possible to cover the skin area covering an artery of the wrist, for example the radial artery 420. When the wearable device 110 is disposed around a wrist of patient's hand 410, the optical sensor 222b is located on the dorsal side of the wrist. The optical sensors 222a and 222b can be configured to be in a continuous contact with the skin of the patient 130.

Figure 4C:
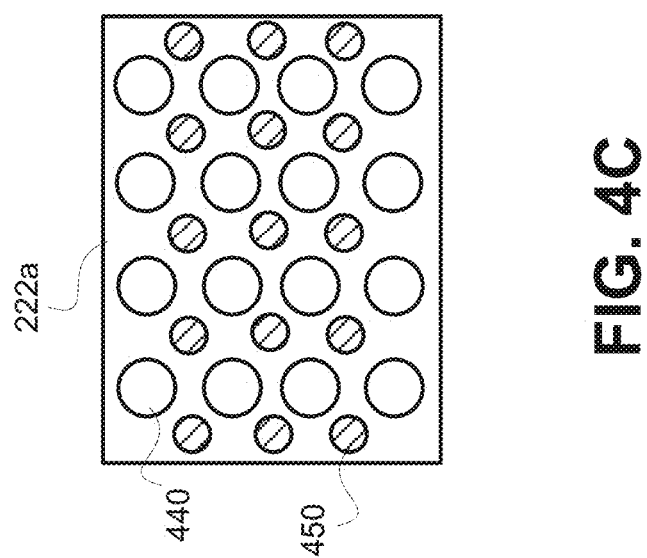
FIG. 4C is a schematic diagram illustrating an example optical sensor.

As shown in FIG. 4C, the optical sensors 222a may include multiple light sensors 440 (photodetectors), to measure the reflected light, and multiple light transmitters 450 (for example, Light Emission Diodes (LEDs)). The number and location of the light sensors 440 and light transmitters 450 can be chosen such that in case of an accidental displacement of the wearable device, at least one of the light sensors is still located sufficiently close to the radial artery. In some embodiments, when measuring the light reflected from the skin and radial artery, a signal from those photoelectric cells that provides the strongest or otherwise determined best output can be selected for further processing in order to obtain medical parameters using methods of pulse (reflectance) oximetry. In certain embodiments, the wearable device 110 can be configured to apply a pre-determined amount of pressure to the wrist each time the user wears the wearable device to allow the same conditions for the reflection of the light from the skin. The optical sensor 222b may include elements analogous to the elements of the optical sensor 222a. The signals measured by optical sensors 222a and 222b can be used to determine oxygen saturation, heart rate, cardiac output, and other parameters using pulse oximetry methods.

Oxygen saturation is the relative proportion (typically expressed as percentage) of oxygen dissolved in blood, as bound to hemoglobin, relative to non-oxygen-bound hemoglobin. Oxygen saturation is important in clinical monitoring of surgical anesthesia, and in monitoring and assessment of various clinical conditions such as COPD and asthma. In healthy individuals, oxygen saturation is over 95%. Direct measurement can be made from arterial blood sample, but drawing blood is an invasive procedure, and, except for a few controlled environments (e.g., during a surgery) cannot be easily performed continuously. Pulse oximetry can yield a quantity called SpO2 (saturation of peripheral oxygen), an accepted estimate of arterial oxygen saturation, derived from optical characteristics of blood using transmission of light through a thin part of a human body (for example, a fingertip or an earlobe (in the most common transmissive application mode)). Reflectance pulse oximetry can be used to estimate SpO2 using other body sites. The reflectance pulse oximetry does not require a thin section of the person's body and is therefore suited to more universal application such as the feet, forehead, and chest, but it has some serious issues due to the light reflected from non-pulsating tissues. When oxygen saturation cannot be measured directly from arterial blood, an indirect measurement can be performed by tracking tissue oxygen saturation. The measurement of oxygen saturation is commonly used to track progression of heart disease or lung disease. When the heart or lungs are not functioning properly, the saturation of oxygen drops in both arterial blood and tissue around the artery. Therefore, tissue oxygen saturation can be measured by sensing the skin color near the radial artery. For example, if the wearable device 110 moves so that optical sensor 222a is not covering the radial artery, measurements of tissue saturation near the radial artery can be used as a backup to provide values for oxygen saturation.

The optical sensor 222a can be configured to measure an infrared wavelength PPG signal $I_a^{ir}$ and a red wavelength PPG signal $I_a^{red}$ near a blood artery of the wrist of the patient (for example, the radial artery 420). The infrared wavelength PPG signal can be obtained by emitting, by the light transmitters 450, an infrared wavelength light and detecting, by the light sensor 440, intensity of infrared light reflected from the skin and blood vessels of the patient. The red wavelength PPG signal can be obtained by emitting, by the light transmitters 450, a red wavelength light and detecting, by the light sensor 440, intensity of red light reflected from the skin and blood vessels of the patient. Similarly, the optical sensor 222a can be configured to measure an infrared wavelength PPG signal $I_b^{ir}$ and a red wavelength PPG signal $I_b^{red}$ from the palmar side of the wrist of patient.

The wearable device 110 can include a gyroscope 430. The gyroscope 430 can be located at any point within the wearable device 110. The gyroscope may include a triple axis Micro Electro-Mechanical Systems (MEMS) gyroscope. The gyroscope 430 can measure rotation around three axes: x, y, and z.

In some embodiments, a gyroscope signal measured by the gyroscope 430 can be analyzed to determine a respiratory rate of a patient. The respiratory rate, which is a vital sign, is typically expressed as the number of breaths per minute. Typical adult resting respiratory rate is about 16-20 breaths per minute. Extreme variations can result from physical or psychological stress. The respiratory rate is often affected in chronic disease states, particularly in pulmonary and cardiovascular disease. Extreme short-term changes may be associated with acute disease episodes, particularly in chronically ill patients.

Figure 5:
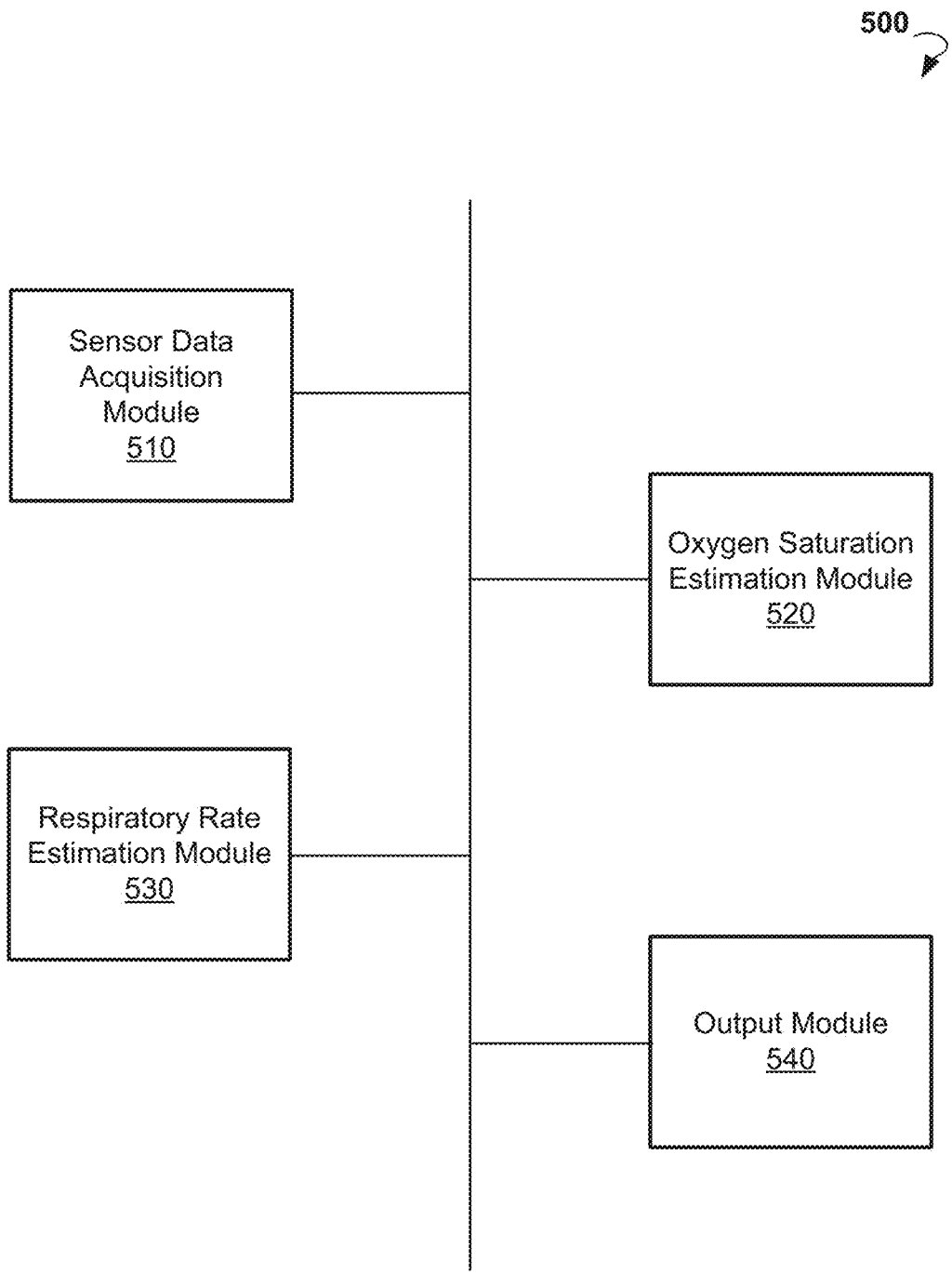
FIG. 5 is a block diagram showing an example system for monitoring medical parameters of a patient.

FIG. 5 is a block diagram showing components of a system 500 for monitoring health status of people suffering from chronic diseases, according to an example embodiment. The system 500 can include a sensor data acquisition module 510, an oxygen saturation estimation module 520, a respiratory rate estimation module 530, and an output module 540. In some embodiments, the modules 510-540 are implemented as chipsets included in the wearable device 110. In other embodiments, the modules 520, 530, and 540 can be stored as instructions in memory of the wearable device 110, mobile device 140, or computing cloud 150, and executed by a processor.

In some embodiments, the sensor data acquisition module 510 is configured to receive and digitize the sensor data. The sensor data acquisition module 510 can include one or more analog-to-digital converters to transform the electrical signals from sensors 120 to digital signals and provide the digital signal to modules 520-540 for further analysis.

In some embodiments, the data processing module is configured to analyze the infrared wavelength PPG signals and the red wavelength PPG signals recorded by the optical sensor 222a and 222b to obtain oxygen saturation using the methods of pulse oximetry.

The methods for pulse oximetry are based on the fact that oxygenated hemoglobin absorbs more infrared light while deoxygenated hemoglobin absorbs more red light. Typically, the methods of the pulse oximetry include calculation of a ratio R defined as follows:

$$R = \frac{\log\left(\frac{I_{max}^{red}}{I_{min}^{red}}\right)}{\log\left(\frac{I_{max}^{ir}}{I_{min}^{ir}}\right)} \quad (1)$$

wherein $I_{max}^{red}$ and $I_{min}^{red}$ are maximum and minimum of red wavelength PPG signal and $I_{max}^{ir}$ and $I_{min}^{ir}$ are maximum and minimum of infrared wavelength PPG signal. The ratio R can indicate a ratio between oxygenated hemoglobin and deoxygenated hemoglobin. The ratio R can be converted to a corresponding oxygen saturation (SpO$_2$) value via an empirically-derived look-up table.

In some embodiments, to take into account contributions due to interaction of light with non-pulsatile tissue, the infrared wavelength PPG signal can be shifted by a parameter $L^{ir}$ and the red wavelength PPG signal can be shifted by a parameter $L^{red}$. The ratio $R_1$ can be then determined as $$R_1(L^{red}, L^{ir}) = \frac{\log\left(\frac{I_{max}^{red} - L^{red}}{I_{min}^{red} - L^{red}}\right)}{\log\left(\frac{I_{max}^{ir} - L^{ir}}{I_{min}^{ir} - L^{ir}}\right)} \quad (2)$$

The ratio $R_1$ can be further used to obtain the oxygen saturation via an empirically-derived look-up table or function. The parameters $L^{red}$ and $L^{ir}$ can be pre-determined in a calibration process. The calibration process may include optimization of $L^{red}$ and $L^{ir}$ to fulfill the equation $R_1(L^{red}, L^{ir})=R_{true}$, wherein the $R_{true}$ is a true value for the ratio R found by a "gold standard" measurement.

Using the infrared wavelength PPG signal $I_a^{ir}$ and the red wavelength PPG signal $I_a^{red}$ recorded by the optical sensor 222a from palmar side of a wrist near a blood artery, the oxygen saturation estimation module 520 may be configured to calculate a ratio $R_a$. Using the infrared wavelength PPG signal $I_b^{ir}$ and red wavelength PPG signal $I_b^{red}$ recorded by the optical sensor 222b from dorsal side of the wrist, the oxygen saturation estimation module 520 may be configured to calculate a ratio $R_b$. The PPG signals $I_a^{ir}$, $I_a^{red}$, $I_b^{ir}$, and $I_b^{red}$ can be recorded substantially simultaneously.

Since the ratio $R_a$ is determined from PPG signals recorded by optical sensor 222a from the palmar side of the wrist near a blood artery, the value of the ratio $R_a$ may be sensitive to location of light transmitters 450 and light sensors 440 relative to the blood artery. Typically, error of value oxygen saturation (SpO$_2$) determined based on ratio $R_a$ decreases with increase of values for oxygen saturations. However, the optical sensor 222a located at the radial artery on the palmar side of the wrist may provide a PPG signals with a Signal-to-Noise Ratio (SNR) higher than the SNR of the PPG signal for optical sensor 222b located on the dorsal side of the wrist. Therefore, a location of an optical sensor near the radial artery is preferable over locations near fingertip or dorsal side of the wrist. Optical sensors located at a fingertip or on the dorsal side of the wrist can measure PPG signals received from small blood vessels. The quality of the PPG measurements received from the small blood vessels may be decreased due to several factors. One of the factors causing decrease in the quality of the PPG measurements includes possible constriction of small vessels due to low ambient temperatures. Another factor causing decrease in the quality of the PPG measurements includes a darker color of the skin covering the small blood vessels, which may lead to a decrease of the SNR in the PPG signals.

The ratio $R_b$ is determined from PPG signals recorded at dorsal side of the wrist, which does not include pulsatile blood vessels. Therefore, the ratio $R_b$ can be assumed to be independent on location of the light transmitters and light sensors of the optical sensor 222b relative to the surface of the dorsal side of the wrist. When PPG signals $I_b^{ir}$, and $I_b^{red}$ recorded by the optical sensor 222b are of a good quality, that is having a high SNR (as defined above), then the ratio $R_b$ obtained using the PPG signals $I_b^{ir}$ and $I_b^{red}$ can be used to calibrate the PPG signals $I_a^{ir}$ and $I_a^{red}$ recorded by the optical sensor 222a.

In some embodiments, the ratio $R_a$ can be found by using the formula (2) and the ratio $R_b$ can be found by using formula (1). The ratio $R_b$ can be further used as $R_{true}$ (the "gold standard" measurement) to optimize the parameters $L^{red}$ and $L^{ir}$ in formula (2). Thus, the PPG signals measured by the optical sensor 222b on the dorsal side of the wrist can be used to calibrate the optical sensor 222a on the palmar side. The calibration process can be carried out each time the patient wears the wearable device 110. The calibration process can be also performed if a value of the oxygen saturation determined by using the PPG signals measured by the optical sensor 222a is outside a pre-determined range.

In some embodiments, the ratio $R_b$ can be used to correct a value for ratio $R_a$. For example, the ratio $R_a$ and ratio $R_b$ can be fused to obtain a ratio R. The ratio R can be further used to determine value of the oxygen saturation via an empirically-derived look-up table.

In some embodiments, a ratio R can be determined as $$R = \alpha R_a + (1-\alpha) R_b \quad (3)$$

wherein $\alpha$ is a weight, $0 < \alpha \le 1$. The weight $\alpha$ can be determined as a function of SNR of PPG signal $I_b^{ir}$ or PPG signal $I_b^{red}$ measured at the palmar side of the wrist. Higher values of the weight $\alpha$ may correspond to higher values of the SNR of PPG signals $I_b^{ir}$, or $I_b^{red}$ since a higher SNR signal is more reliable for determining ratio R. A weighted average of the ratio $R_a$ and ratio $R_b$ can provide a better estimate for the ratio R because measurement errors of the optical sensor 222a and 222b are independent of each other. At the same time, the ratio $R_a$ can be given a larger weight because a measurement obtained on the palmar side of the wrist and near the radial artery may provide more information for core blood pressure and oxygen saturation than In some other embodiments, weight $\alpha$ can be determined as a function of a perfusion index. The perfusion index is a ratio of the pulsatile blood flow to the non-pulsatile static blood flow in patient's peripheral tissue. The perfusion index can be estimated based on a PPG signal $I_b^{ir}$ or a PPG signal $I_b^{red}$ measured at the dorsal side of the wrist.

Figure 6A:
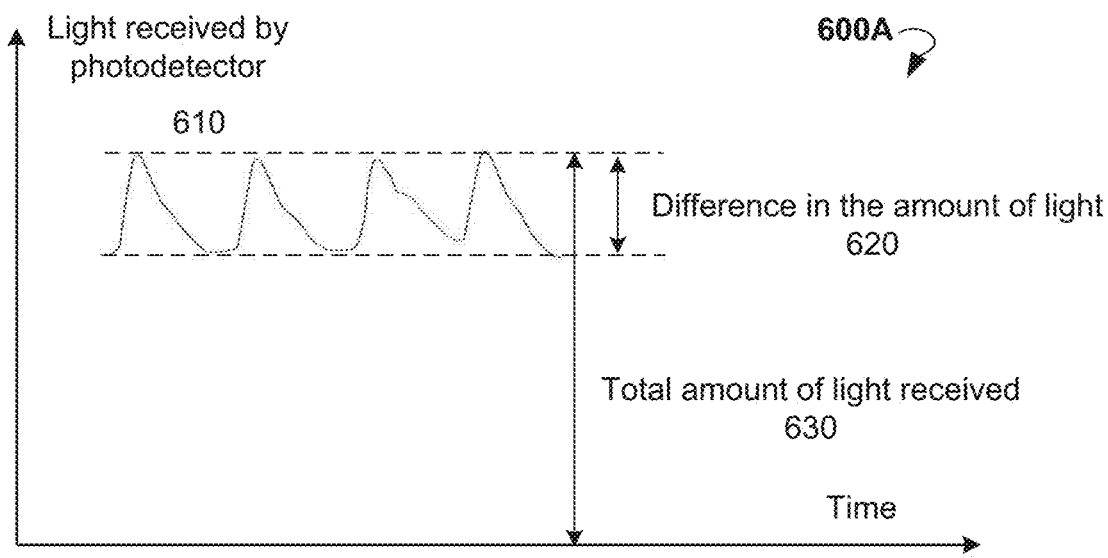
FIG. 6A is a plot of an example PPG signal.

FIG. 6A shows a plot 600A of an example PPG signal 610 which represents an amount of light received by a photodetector of optical sensor 222b. The perfusion index can be calculated as a ratio of difference 620 of the amount of light received by the photodetector between vasoconstriction and vascular dilation to the total amount 630 of light received by the photodetector. Typically, the larger the perfusion index, the more accurate the measurement of oxygen saturation. Therefore, the perfusion index can be used as an indicator of quality of the PPG signal.

If the perfusion index determined based on PPG signals PPG signal $I_b^{ir}$ and PPG signal $I_b^{red}$ measured at the dorsal side of the wrist are higher than a pre-determined threshold, the ratio $R_b$ obtained using the PPG signals $I_b^{ir}$ and $I_b^{red}$ can be used to correct the ratio $R_a$ using formula (3). Furthermore, if the perfusion index determined based on the PPG signal $I_b^{ir}$ and PPG signal $I_b^{red}$ measured at the dorsal side of the wrist are higher than a pre-determined threshold, the ratio $R_b$ can be also used to determine parameters $L^{red}$ and $L^{ir}$ in formula (2) for shifting PPG signals $I_a^{red}$ and $I_a^{ir}$ and, thereby, calibrate the optical sensor 222a disposed at the palmar side of the wrist.

Figure 6B:
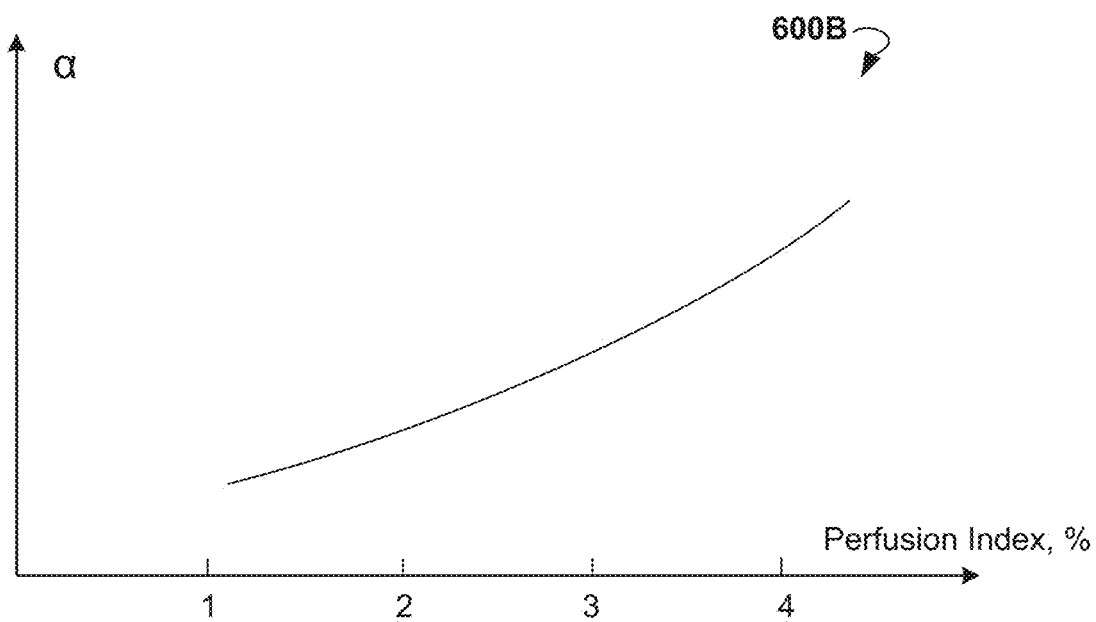
FIG. 6B shows an example function 600 for determining the weight $\alpha$ based on the value of a perfusion index.

FIG. 6B shows an example function 600B for determining the weight α based on the value of perfusion index. The value of the perfusion index can be found based on the PPG signal $I_b^{ir}$ or the PPG signal $I_b^{red}$ measured at the dorsal side of wrist of a patient. The shape of function 600 can be determined in a calibration process. The weight α increases with an increase of the value for the perfusion index.

In some embodiments, the respiratory rate estimation module 530 is configured to analyze the gyroscope signal (rotation around three axes x, y, and z) measured by the gyroscope 430 at a wrist to obtain respiratory rate of a patient. It was found in tests performed by inventor that the gyroscope signal measured at the wrist of the patient includes data due to a cyclical motion of the chest of the patient. During the tests, a gyroscope signal measured by a gyroscope disposed at a wrist of a patient and a reference gyroscope signal measured by a gyroscope disposed in a chest strap at the chest of the patient were recorded simultaneously. A spectral analysis of the gyroscope signal measured at the wrist and the reference gyroscope signal measured at the chest were performed. A comparison of the spectra of the signals shows that the gyroscope signal measured at the wrist contains a frequency corresponding to the number of breaths of patient as determined based on the reference gyroscope signal measured at the chest.

Figure 7:
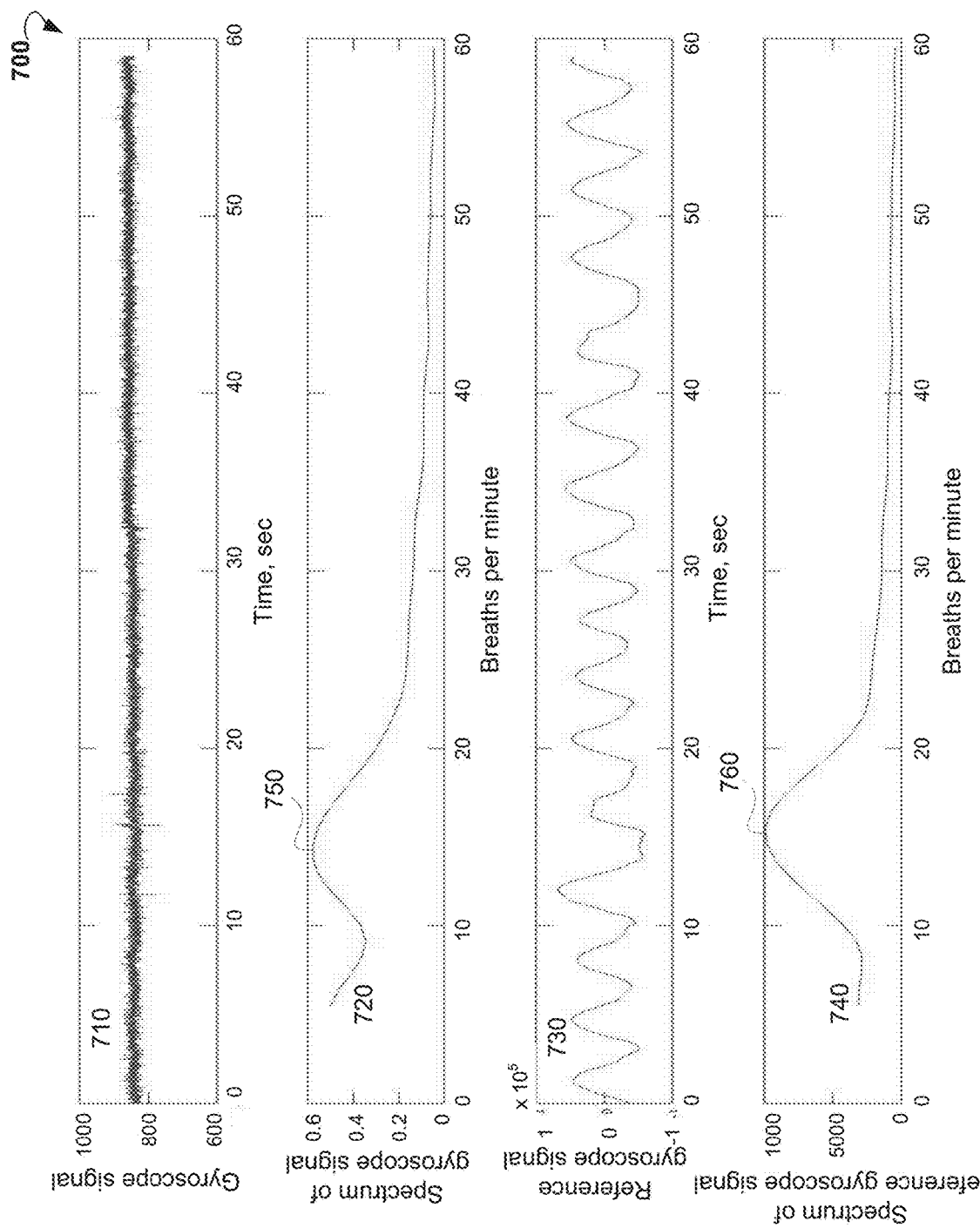
FIG. 7 shows plots of a gyroscope signal, spectrum of the gyroscope signal, reference signal, and spectrum of the reference signal.

FIG. 7 shows plot 700 of example gyroscope signal 710 measured at a wrist, spectrum 720 of the gyroscope signal 710, reference gyroscope signal 730 measured at the chest, and spectrum 740 of the reference gyroscope signal 730. The spectrum 720 of the gyroscope signal 710 includes a peak 750, which corresponds to a peak 760 in spectrum 740 of the reference gyroscope signal 730. The frequency at the peak 750 corresponds to the respiratory rate.

Figure 8:
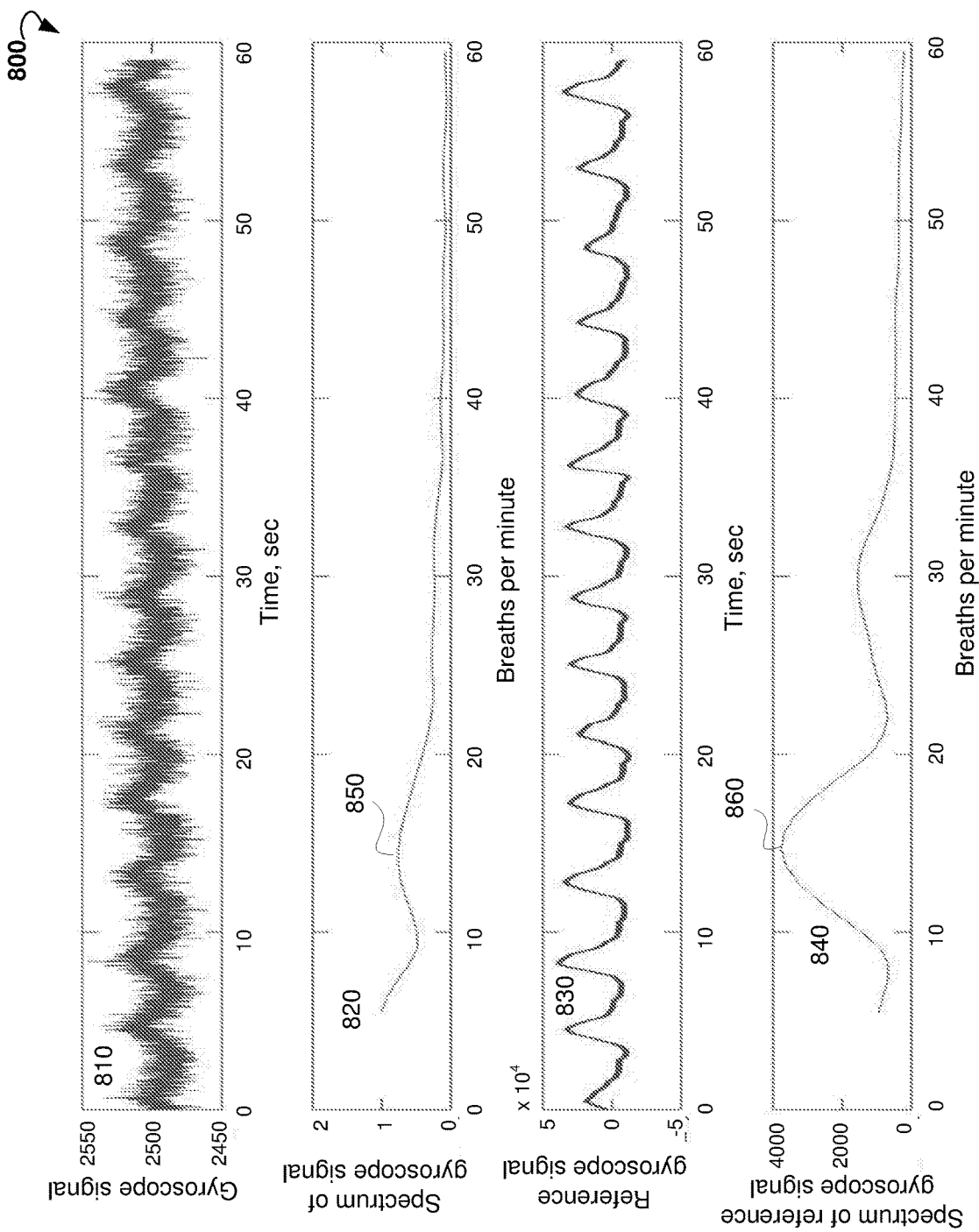
FIG. 8 shows plots of another gyroscope signal, spectrum of another gyroscope signal, another reference gyroscope signal, and spectrum of another reference gyroscope signal.

FIG. 8 shows plot 800 of example gyroscope signal 810 measured at a wrist, spectrum 820 of the gyroscope signal 810, reference gyroscope signal 830 measured at the chest, and spectrum 840 of the reference gyroscope signal 830. The SNR of gyroscope signal 810 is higher than SNR of the gyroscope signal 710 shown in FIG. 7. The spectrum 820 of the gyroscope signal 810 includes a peak 850 which corresponds to peak 860 in spectrum 840 of the reference gyroscope signal 830. The frequency at the peak 850 corresponds to the respiratory rate.

The respiratory rate estimation module 530 may receive the gyroscope signal measured by the gyroscope 430 at the wrist of the patient and perform the spectral analysis of the gyroscope signal to obtain a spectrum of the gyroscope signal in a pre-determined range. The pre-determined range can be selected to cover a range of typical values for the respiratory rate of a human (for example, 6-18 breaths per minute). For example, the pre-determined range may include a range of 0 to 50 breaths per minute. In some embodiments, the spectral analysis may include fast Fourier transform, averaged periodograms (Bartlett's method), Welch's method, least-squares spectral analysis, and so forth.

The respiratory rate estimation module 530 can be further configured to determine a position of a peak in the spectrum that corresponds to the number of breaths of a patient per minute (the respiratory rate). In some embodiments, the respiratory rate estimation module 530 can be configured to select the strongest peak in the pre-determined range. As seen in FIG. 7 and FIG. 8, the spectrum of the gyroscope signal can be contaminated by a noise caused by movement of the patient. Typically, the noise is of a low frequency. Therefore, in the spectrum, the frequencies caused by the noise may interfere with the frequency corresponding to the respiratory rate.

The signal s(t) representing motion of breathing can be described by formula:

$$s(t)=\Sigma_{n=1}^{\infty}A_n f(n*\omega*t) \quad (4)$$

wherein f is a periodic function, ω is a fundamental frequency, and $A_n$ are descending amplitudes. In a frequency domain, the signal s(t) is represented by peaks at frequencies n*ω, wherein amplitudes of the peaks descend with the increase of n. This pattern can be searched in a spectrum of the gyroscope signal measured by the gyroscope at a wrist of patient to confirm that a correct peak was assigned to the respiratory rate.

After determining the strongest peak, the respiratory rate estimation module 530 can confirm that the strongest peak in the spectrum represents breathing of the patient and not caused by movement noise of the patient. The respiratory rate estimation module 530 can be configured to determine that the spectrum includes one or more further peaks with descending amplitudes, such as the further peaks corresponding to frequencies n*ω, wherein ω is a frequency corresponding to the strongest peak, and n is a natural number. Based on the determination, the respiratory rate estimation module 530 can assign value ω to the value of the respiratory rate.

In some embodiments, the output module 540 is configured to provide reports and alert messages regarding a health status of the patient. The output module 540 may be configured to display via a graphical display system of the wearable device 110 or the mobile device 140. The output module 540 may determine that the respiratory rate of the patient is near or outside of a typical range (for example, 6-18 breaths per minute). The output module 540 may also determine that the value of oxygen saturation of the patient is below a pre-determined threshold. In response to the determination, the output module 540 may provide an alert message to the patient via a graphical display system of the wearable device 110 or/and mobile device 140. The alert message may include an advice to take medication or contact a doctor. The output module may also send a warning message, via the communication unit of the wearable device 110 and/or mobile device 140, to a computing device of a relative, a doctor, or a caretaker of the patient.

FIG. 9 is a flow chart diagram showing example method 900 for monitoring oxygen saturation of a patient. The method 900 may be implemented in system 100. In block 910, the method 900 may commence with measuring at a palmar surface of a wrist of the patient, by a first optical sensor, a first red wavelength PPG signal and a first infrared wavelength PPG signal. The first optical sensor can be embedded into a wearable device disposed around the wrist of the patient.

In block 920, the method 900 may proceed with measuring, at a dorsal surface of the wrist, by a second optical sensor disposed in the wearable device, a second red wavelength PPG signal and a second infrared wavelength PPG signal. The second red wavelength PPG signal and the second infrared wavelength PPG signal can be measured substantially simultaneously with the first red wavelength PPG signal and the first infrared wavelength PPG signal.

In block 930, the method 900 may continue with determining, by a processor communicatively connected to the first optical sensor and the second optical sensor and based on the first red wavelength PPG signal and the first infrared wavelength PPG signal, a first ratio for obtaining an oxygen saturation. In block 940, the method 900 may determine, by the processor and based on the second red wavelength PPG signal and the second infrared wavelength PPG signal, a second ratio for obtaining the oxygen saturation.

In block 950, the method 900 may determine, by the processor and based on the first ratio and the second ratio, a third ratio for obtaining an oxygen saturation. In block 960, the method 900 may determine, by the processor and based on the third ratio, a value of the oxygen saturation. In block 970, the method 900 may include providing, by the processor and based on the value of the oxygen saturation, a message regarding a health status of the patient. The message may include a warning against upcoming episode or worsening of a chronic disease of the patient, for which the oxygen saturation is one of the indicators. Upon receiving such a warning, preventive measures can be taken to reduce the severity of upcoming or worsening of the chronic disease. The message may include an advice to take a medicine or to contact a doctor.

FIG. 10 is a flow chart diagram showing an example method 1000 for monitoring respiratory rate of a patient. The method 1000 may be implemented in system 100. In block 1010, the method 1000 may commence with providing, by a gyroscope of a wearable device disposed on a wrist of a patient, a gyroscope signal indicative of a motion of the patient. The gyroscope can be communicatively coupled with a processor. In block 1020, the method 1000 may proceed with performing, by the processor, a spectral analysis of the gyroscope signal to obtain a spectrum in a pre-determined frequency range, the pre-determined frequency range covering a normal respiratory rate range. In block 1030, the method 1000 may determine, by the processor, a position of a peak in the spectrum to obtain a value for a respiratory rate. In block 1040, the method 1000 may provide, by the processor and based on the value of the respiratory rate, a message regarding the health status of the patient. In some embodiments, the method 1000 may determine, by the processor, that the value of the respiratory rate is outside of the normal respiratory rate range and provide, by the processor, an alert message regarding the health status of the patient based on the determination that the value of the respiratory rate is outside of the normal respiratory rate range. The alert message may include a warning against upcoming or worsening of a chronic disease from which the patients suffers, for which respiratory rate is one of the indicators. Upon receiving the message, preventive measures can be taken to reduce the severity of upcoming or worsening of a chronic disease. The message may include an advice to take a medication or to contact a doctor.

The present technology is described above with reference to example embodiments. Therefore, other variations upon the example embodiments are intended to be covered by the present disclosure.

What is claimed is:

1. A system for monitoring a respiratory rate of a patient, the system comprising:
   a wearable device configured to be disposed around a wrist of the patient, the wearable device comprising:
   a gyroscope configured to provide a gyroscope signal indicative of a motion of the patient;
   a first optical sensor configured to measure, at a palmar surface of the wrist, a first red wavelength photoplethysmography (PPG) signal and a first infrared wavelength PPG signal; and
   a second optical sensor configured to measure, at a dorsal surface of the wrist, a second red wavelength PPG signal and a second infrared wavelength PPG signal; and
   a processor communicatively connected to the gyroscope, the first optical sensor, and the second optical sensor, the processor being configured to:
   perform a spectral analysis of the gyroscope signal to obtain a spectrum in a pre-determined range, the pre-determined range covering a normal respiratory rate range;
   determine a position of a peak in the spectrum to obtain a value for the respiratory rate;
   provide, based on the value of the respiratory rate, a message regarding a health status of the patient;
   determine, based on the first red wavelength PPG signal and the first infrared wavelength PPG signal, a first ratio for obtaining an oxygen saturation;
   determine, based on the second red wavelength PPG signal and the second infrared wavelength PPG signal, a second ratio for obtaining oxygen saturation;
   determine, based on the first ratio and the second ratio, a third ratio for obtaining an oxygen saturation;
   determine, based on the third ratio, a value of the oxygen saturation; and
   provide, based on the value of the oxygen saturation, a further message regarding the health status of the patient.

2. The system of claim 1, wherein the spectral analysis is performed by a method of averaged periodograms.

3. The system of claim 1, wherein the normal respiratory rate range includes 6 to 18 breaths per minute.

4. The system of claim 1, wherein the processor is further configured to determine a strongest amplitude peak in the spectrum to obtain the value for the respiratory rate.

5. The system of claim 1, wherein the processor is further configured to:
   determine that the spectrum includes one or more further peaks with descending amplitudes, the one or more further peaks corresponding to frequencies $n*\omega$, wherein $\omega$ is a frequency corresponding to the peak, and n is a natural number; and
   based on the determination, assign w to the value of the respiratory rate.

6. The system of claim 1, wherein the third ratio is determined by formula $R=\alpha R_a+(1-\alpha)R_b$, wherein the $\alpha$ is a weight between 0 and 1, the $R_a$ is the first ratio, and the $R_b$ is the second ratio.

7. The system of claim 6, wherein the weight a is a function of a perfusion index determined based on the second red wavelength PPG signal or the second infrared wavelength PPG signal.

8. The system of claim 7, wherein the weight a increases when the perfusion index increases.

9. The system of claim 1, wherein the first optical sensor is configured to measure the first red wavelength PPG signal and the first infrared wavelength PPG signal substantially near a radial artery of the wrist.

10. The system of claim 1, further comprising one or more electrical sensors, the one or more electrical sensors being configured to measure an electrocardiogram activity of the patient.

11. A method for monitoring a respiratory rate of a patient, the method comprising:
providing, by a gyroscope disposed in a wearable device, a gyroscope signal indicative of a motion of the patient, wherein the wearable device is configured to be worn around a wrist of the patient;
measuring, at a palmar surface of the wrist of the patient, by a first optical sensor of the wearable device, a first red wavelength photoplethysmography (PPG) signal and a first infrared wavelength PPG signal;
measuring, at a dorsal surface of the wrist, by a second optical sensor of the wearable device, a second red wavelength PPG signal and a second infrared wavelength PPG signal, the first optical sensor and the second optical sensor being communicatively coupled to a processor;
performing, by a processor communicatively coupled with the gyroscope, a spectral analysis of the gyroscope signal to obtain a spectrum in a pre-determined range, the pre-determined range covering a normal respiratory rate range;
determining, by the processor, a position of a peak in the spectrum to obtain a value for the respiratory rate;
providing, by the processor and based on the value of the respiratory rate, a message regarding a health status of the patient;
determining, by the processor and based on the first red wavelength PPG signal and the first infrared wavelength PPG signal, a first ratio for obtaining an oxygen saturation;
determining, by the processor and based on the second red wavelength PPG signal and the second infrared wavelength PPG signal, a second ratio for obtaining the oxygen saturation;
determining, by the processor and based on the first ratio and the second ratio, a third ratio for obtaining an oxygen saturation;
determining, by the processor and based on the third ratio, a value of the oxygen saturation; and
providing, by the processor and based on the value of the oxygen saturation, a further message regarding the health status of the patient.

12. The method of claim 11, wherein the spectral analysis is performed by a method of averaged periodograms.

13. The method of claim 11, wherein the normal respiratory rate range is 6 to 18 breaths per minute.

14. The method of claim 11, wherein the determining the position of the peak includes determining a strongest amplitude peak in the spectrum.

15. The method of claim 11, further comprising, after the determining the position of the peak:
determining, by the processor, that the spectrum includes one or more further peak with descending amplitudes, the one or more further peak corresponding to frequencies $n*\omega$, wherein $\omega$ is a frequency corresponding to the peak, and n is a natural number; and
based on the determination, assigning, by the processor, the w to the respiratory rate.

16. The method of claim 11, wherein the third ratio is determined by formula $R=\alpha R_a+(1-\alpha)R_b$, wherein the $\alpha$ is a weight between 0 and 1, $R_a$ is the first ratio, and the $R_b$ is the second ratio.

17. The method of claim 16, wherein:
the weight $\alpha$ is a function of perfusion index determined based on the second red wavelength PPG signal or the second infrared wavelength PPG signal; and
the weight $\alpha$ increases when the perfusion index increases.

18. The method of claim 11, wherein the first optical sensor is configured to measure the first red wavelength PPG signal and the first infrared wavelength PPG signal substantially near a radial artery of the wrist.

19. The method of claim 11, further comprising measuring, by one or more electrical sensors, an electrocardiogram activity of the patient.

20. A non-transitory computer-readable storage medium having embodied thereon instructions, which when executed by a processor, perform steps of a method, the method comprising:
acquiring a gyroscope signal indicative of a motion of a patient, the gyroscope signal being measured by a gyroscope disposed in a wearable device configured to be worn around a wrist of the patient, the gyroscope communicatively coupled with the processor;
acquiring a first red wavelength photoplethysmography (PPG) signal and a first infrared wavelength PPG signal, the signals being measured by a first optical sensor disposed in the wearable device to perform measurements on a palmar surface of the wrist;
acquiring a second red wavelength PPG signal and a second infrared wavelength PPG signal, the signals being measured by a second optical sensor disposed in the wearable device to perform measurements on a dorsal surface of the wrist, wherein the first optical sensor and the second optical sensor are communicatively coupled with the processor;
performing a spectral analysis of the gyroscope signal to obtain a spectrum in a pre-determined range, the pre-determined range covering a normal respiratory rate range;
determining a position of a peak in the spectrum to obtain a value for a respiratory rate;
providing, based on the value of the respiratory rate, a message regarding a health status of the patient;
determining, based on the first red wavelength PPG signal and the first infrared wavelength PPG signal, a first ratio for obtaining an oxygen saturation;
determining, based on the second red wavelength PPG signal and the second infrared wavelength PPG signal, a second ratio for obtaining oxygen saturation;
determining, based on the first ratio and the second ratio, a third ratio for obtaining an oxygen saturation;
determining, based on the third ratio, a value of the oxygen saturation; and
providing, based on the value of the oxygen saturation, a further message regarding the health status of the patient.

* * * * *